United States Patent [19]

Szejtli et al.

[11] 4,272,276

[45] Jun. 9, 1981

[54] METHOD FOR THE CONTROL OF GERMINATION OF PLANT SEEDS AND GROWTH OF THE SEEDLINGS

[75] Inventors: József Szejtli; Magda Tétényi née Erdösi; Peter Tetenyi, all of Budapest, Hungary

[73] Assignee: Chinoin Gyogyszer es Vegyeszeti Termekek Gyara Rt, Budapest, Hungary

[21] Appl. No.: 40,957

[22] Filed: May 21, 1979

[30] Foreign Application Priority Data

May 23, 1978 [HU] Hungary .............................. CI-1830

[51] Int. Cl.³ .......................................... A01N 43/16
[52] U.S. Cl. ........................................ 71/76; 71/88; 47/57.6
[58] Field of Search ................ 71/77, 76, 88; 536/103

[56] References Cited

U.S. PATENT DOCUMENTS

| 2,553,577 | 5/1951 | Hale et al. ................................. 71/77 |
| 2,827,452 | 3/1958 | Schlenk et al. ....................... 536/103 |
| 3,140,184 | 7/1964 | Robbins .............................. 536/103 |
| 3,640,847 | 2/1972 | Armbruster et al. ................ 536/103 |
| 4,067,141 | 1/1978 | Matsunaga et al. ...................... 71/77 |

OTHER PUBLICATIONS

Florescu et al., Chemical Abstracts, vol. 80: 58944d, (1974).
Misato et al., Chemical Abstracts, vol. 82: 120072q, (1975).

*Primary Examiner*—Paul M. Coughlan, Jr.
*Attorney, Agent, or Firm*—Karl F. Ross

[57] ABSTRACT

A method of controlling seed germination and growth of the seedlings which comprises contacting plant seeds with a liquid or solid dextrin.

5 Claims, No Drawings

METHOD FOR THE CONTROL OF GERMINATION OF PLANT SEEDS AND GROWTH OF THE SEEDLINGS

FIELD OF THE INVENTION

The present invention relates to a method of delaying the germination of plant seeds and for stimulating the growth of the sprouting plants developed by delayed germination by using linear and cyclic dextrins or various mixtures thereof.

The invention also deals with compositions having the above effect.

BACKGROUND OF INVENTION

Natural inhibitors of germination are various substances in the seed or in nature, such as "blastocholines", for example, lactones selected from scopoletin, parascorbic acid, daphnetin, coumarin; phenol derivatives, such as phloridzin, chlorogenic acid, juglone, cinnamic acid, coffee acid, ferulic acid, mustard oil glycosides, such as allyl-, and beta-phenylisothiocyanate; aldehydes selected from citral aldehyde cinnamic aldehyde, salicyl aldehide and benzaldehyde and the newly discovered abscisic acid.

Germination is usually controlled in practice by using thiourea, which stimulates germination and by using coumarin, which inhibits germination.

DESCRIPTION OF THE INVENTION

We have now found that cyclodextrins themselves and in mixture with each other or with linear dextrins show a significant germination inhibiting effect on germinating seeds followed by a growth regulating effect on the seeds and the sprouting plants. We have also observed that depending upon the plant species and the conditions of the application (duration of treatment, temperature) different plant growth regulating effects could be achieved, in the range from 90% germination inhibition to about 50% plant growth stimulation, these effects can be obtained corresponding to the desired effect.

The physiological basis of the mechanism of the experienced germination inhibition can be deduced from the earlier observations that cyclodextrins are competitive inhibitors of certain enzymes, such as amylases (J. A. Chem. Soc., 82, 3229; (1960) and also the fact that the $\beta$-amylase enzyme of batata belonging to higher plants is more sensitive to cyclodextrin inhibition than the enzyme of certain bacteria, such as Bacillus polymyxa (Mol. Cell. Biochem., 7, 127; (1975).

Cyclodextrins, also called Schardinger dextrins, cycloamyloses, or cycloglucans are cyclic compounds consisting of glucopyranose units. $\alpha$-Cyclodextrin contains 6, $\beta$-cyclodextrin contains 7, and $\gamma$-cyclodextrin has 8 glucopyranose units. Cyclodextrins are prepared from starch by using cyclodextrin-trans glucosylase enzyme.

Linear dextrins, called also open chained dextrins are macromolecular fragments obtained by direct decomposition of starch by acid, enzyme, or by thermic decomposition thereof, are known also as acid dextrins or roast dextrins.

According to the invention plant seeds are contacted before sowing and/or simultaneously with the sowing with liquid and/or solid dextrins, such as linear and/or $\alpha$-, $\beta$- or $\gamma$-cyclodextrins and/or ad libitum mixtures thereof, if together with us other agents applied in plant cultivation, such as herbicides, fungicides, insecticides, and/or fertilizers and/or trace elements.

The composition of the invention contains 0.1 to 95% $\alpha$-, $\beta$- or $\gamma$-cyclodextrin and/or linear dextrin or a mixture thereof (a) in the form of a dust mixture, if desired associated with the usual carriers, diluents or other excipients, herbicides, fungicides, or insecticides and/or fertilizers and/or trace elements or (b) in the form of aqueous or aqueous-ethanolic solution, if desired associated with fungicides, herbicides or insecticides.

As cyclodextrins $\alpha$-, $\beta$- and $\gamma$-cyclodextrin may be used separately or in any mixture thereof. Such a mixture is formed for example from starch by using cyclodextrin-transglucosylase enzyme. Cyclodextrin-linear cyclodextrin mixture are thus obtained.

The treatment of the seeds by dextrins may be carried out by wet or dry processes. In the wet process the seeds are preferably soaked with an aqueous solution of dextrins. The solutions may contain the conventionally used excipients as well. With the dry process one can apply the seeds to the soil with a dry mixture of the dextrins containing optionally other agents as well. In the soil the treatment takes place after sowing upon the humidity of the soil. It is also possible to prepare dragees before sowing by methods known per se from the sowing-seed-dextrin mixture containing optionally other substances as well or to provide dragees containing the seeds without dextrins with a coating containing dextrins.

The dragees are prepared by methods known per se in a dragee pan by using wood flour, perlite, polyacrylonitrile, or carboxymethyl-cellulose the method comprising dissolving the linear or cyclodextrins or a mixture thereof in the aqueous solution of the component used as binding agent. Thus the amount of linear and cyclodextrins per seed unit may be precisely calculated.

In the course of sowing the seeds and the dextrin or dextrin mixture containing optionally other agents can be stored separately in the sowing machine. They are then brought into contact only upon applying them into the soil.

According to the invention the seeds may be treated with dextrins also by admixing the dextrins with other ingredients, such as herbicides, fungicides, and/or insecticides and/or fertilizers and/or components thereof, for example trace elements.

Though every dextrin is suitable for the sowing-seed treatment according to the invention, we have found that if germination takes place at a higher temperature than $+10°$ C., $\alpha$-cyclodextrin is preferred, whereas at a germination temperature below $+10°$ C., $\beta$-cyclodextrin is preferably employed.

The method of treatment according to the invention prevents frost-bite which often occurs in the autumn sowings in the case of too early germination of the plants, and prolongs the vegetation period of species without an autumn variant, thus making possible seed cultivation of plants having a long cultivation time. If the pre-emergence treatment of the undesired vegetation is carried out simultaneously with the sowing of the treated seeds, then the selectivity of the herbicidal agent increases as the seeds of cultivated plants of delayed germination are not very sensitive to herbicides.

As in the process of germination the enzymatic mobilization of reserve nutriments is of critical importance.

The germination of seeds having high starch content have been examined (Triticale, barley, rye). The germination percentage has not been significantly influenced by the cyclodextrin treatment, but the process of the germination has been considerably delayed. The observed activity is completely irreversible, not due to toxicity, cyclodextrin does not "intoxicate" the germinating seeds.

When the developed seedlings are examined after the seeds have been treated, the growth inhibition was found to vary according to the duration of the treatment as follows: treatments lasting 4, 24, 48 and 72 hours were carried out, the most significant germination inhibiting activity was shown after 48 hours of treatment. The extent of the inhibition of the germination is highly influenced by the temperature as well. Among the three temperatures: $+28°$ C., $+10°$ C. and $+3°$ C., the lowest extent of inhibition of germination could be observed at $+10°$ C., this result is of great significance from the point of view of the utility of the process of the invention.

When seeds containing volatile oil (anise) are used it is found that cyclodextrin causes less growth inhibition than in the case of plants having seeds of starch content, on the contrary at a lower temperature after several days an expressed growth stimulation occurred upon treatment.

The growth stimulating effect of cyclodextrins has been found in the straight growth, Avena coleoptyl section test as well. In the test $10^{-2}$ M $\beta$-cyclodextrin induced 51.2% growth stimulation, $10^{-3}$ M $\beta$-cyclodextrin however induced 17.1% growth inhibition, but even $10^{-4}$ M $\beta$-cyclodextrin induced a 4.9% elongation growth inhibition.

The method of seed-treatment according to the invention may preferably be utilized in the following fields:

(a) Under temperate zone conditions where spring barley, spring wheat, and moan develop rapidly giving a low crop yield; this is why autumn species are generally employed. Spring barley and wheat species are made suitable for autumn sowing by the present invention. In these cases the seeds are placed in the soil in the autumn and due to the retarded germination they are not sensitive to cold while in spring the most favorable development is ensured for the plants.

(b) For those species which do not exist in an autumn variant and whose cultivation is not successful because the long cultivation time of the plants presents a generative period during the vegetative period. Among such plants generally the umbellate plants, such as sweet caraway, coriander and anise may be mentioned. Autumn sowing preceded by the treatment according to the invention prolongs the vegetative period of such plants.

(c) Autumn crops, such as autumn rye if not sown in early autumn (to get strengthened) but later, no stem fastening, growth retarding treatment is needed and the plants will have low stems protecting them against lodging.

(d) With pre-emergence treatment against undesired vegetation for example in wheat, barley, corn, poppy, Digitalis species simultaneously with the sowing of the seeds treated according to the invention; a delay in several days of germination protects the plant against detrimental effects ("antidotum activity") and the process will be simplified, the selectivity of herbicidal agents will be increased.

This process is not based upon intoxication. After the delayed germination in most of the cases the seedling growth is stimulated. This activity is shown by the Examples.

According to investigations cyclodextrins influence particularly germination and the growth of the seedlings in the initial period of the plant growth process, when food mobilization is of great significance. This may be explained partly by the fact, that cyclodextrins are competitive inhibitors of the amylases taking part in the starch decomposition, but the hormonal regulation is probably also effected.

Autumn sowing of spring crops with inhibited germination according to the invention gives a 20% increase of the crop yields, and the treatment of autumn crops of low stem may yield a significant cost-decrease. Autumn sowing of spring species with a long cultivation period can result in a 50-100% increase of the crop in the seed cultivation and by using the method simultaneously with herbicidal treatment at least a 10% crop-security increase may be achieved.

A further advantage of the process of the invention is the fact that the used compounds are quite safe, do not pose any danger of intoxication and do not pollute the environment. The substances decompose without any residue or are utilized by the developing plants.

SPECIFIC EXAMPLES

Further details of the invention may be found in the following Examples which serve merely as illustration and not as limitations.

EXAMPLE 1

Growth inhibition of spring barley (Hordeum vulgare L.cv. 'MK 42') at $+28°$ C.

30 barley seeds were placed to two 9 cm. diameter Petri-dishes on filter papers. Onto the Petri-dishes (a) 5 ml. of $10^{-2}$ M $\alpha$-cyclodextrin solution,
(b) 5 ml. of $10^{-2}$ M $\beta$-cyclodextrin solution,
(c) 5 ml. of 1% linear dextrin solution (roast dextrin),
(d) 5 ml. of distilled water as control were pipetted.

The seeds were germinated at $+28°$ C. in a thermostat, and after 48 hours after washing the seeds were placed on a filter-paper; soaked in distilled water and after 24 hours (at 3 days' age) and under similar conditions at 6 days' age the total length of 30—30 seed sprouts of roots was measured. The test was thrice repeated. The averages of 3—3 simultaneous test data gives one experimental variant. The experiment is repeated in every case. The values of the treated seeds were compared with the growth of the control plants, i.e. where inhibition is 0%.

EXAMPLE 2

Growth inhibition of Triticale (strain 64) at $+28°$ C.

The test was carried out as described in Example 1, but with Triticale seeds were employed. The results are shown in Table II.

EXAMPLE 3

Growth inhibition of autumn rye (Secale cereale L. cv. "Petkus tetra") at +28° C.

The experiments were carried out as described in Example 1 but with autumn rye seeds. The results are given in Table III.

EXAMPLE 4

Growth regulation of corn (Zea mays L.cv. 'Aranymazsola') at +28° C.

The experiments were carried out as described in Example 1 but with corn seed. The results are shown in Table IV.

TABLE II

|  |  | α | β | Control |
|---|---|---|---|---|
|  |  | cyclodextrin |  |  |
| 30 plants |  |  |  |  |
| total length of the sprouts (mm.) | after 3 days | 311 | 584 | 732 |
| total length of the sprouts (mm.) | after 6 days | 1221 | 2027 | 2390 |
| inhibition % | after 3 days | 57.5 | 20.2 | 0 |
| inhibition % | after 6 days | 48.9 | 15.2 | 0 |
| total length of the roots (mm.) | after 3 days | 1143 | 1340 | 3046 |
| total length of the roots (mm.) | after 6 days | 2449 | 3663 | 4668 |
| inhibition % | after 3 days | 62.5 | 56.0 | 0 |
| inhibition % | after 6 days | 47.5 | 21.5 | 0 |

TABLE III

|  |  | α | β | linear dextrin | control |
|---|---|---|---|---|---|
|  |  | cyclodextrin |  |  |  |
| 30 plants |  |  |  |  |  |
| total length of the sprouts (mm.) | after 3 days | 253 | 332 | 438 | 639 |
| total length of the sprouts (mm.) | after 6 days | 828 | 1392 | 1403 | 1888 |
| inhibition % | after 3 days | 60.4 | 48.0 | 31.5 | 0 |
| inhibition % | after 6 days | 56.1 | 26.3 | 25.7 | 0 |
| total length of the roots (mm.) | after 3 days | 2257 | 2463 | 2070 | 4226 |
| total length of the roots | after 6 days | 3187 | 4490 | 4240 | 7368 |
| inhibition % | after 3 days | 46.6 | 41.8 | 51.0 | 0 |
| inhibition % | after 6 days | 56.7 | 39.1 | 42.5 | 0 |

TABLE IV

|  |  | α | β | linear* dextrin | control |
|---|---|---|---|---|---|
|  |  | cyclodextrin |  |  |  |
| 30 plants |  |  |  |  |  |
| total length of the sprouts (mm) | after 3 days | 130 | 147 | 252 | 188 |
| total length of the sprouts (mm) | after 6 days | 924 | 1070 | 1720 | 1210 |
| inhibition % | after 3 days | −30.9 | −21.8 | +34.0 | 0 |
| inhibition % | after 6 days | −23.6 | −11.6 | +42.1 | 0 |
| total length of the roots (mm) | after 3 days | 1189 | 940 | 1804 | 1259 |
| total length of the roots (mm) | after 6 days | 1447 | 1204 | 3085 | 1789 |
| inhibition % | after 3 days | −5.6 | −25.3 | +43.3 | 0 |
| inhibition % | after 6 days | −19.1 | −32.7 | +72.4 |  |

* +stands for stimulation

EXAMPLE 5

Growth regulation of spring barley (Hordeum vulgare L.cv. 'MK 42') at +10° C.

The test is carried out as described in the previous Examples whereafter the seeds soaked in the solutions in Petri-dishes are placed to a refrigerator of +10° C. and after 8 days the sprout and root-length of the seedling are measured. The measured data are shown in Table V.

TABLE V

|  | α | β | linear dextrin | control |
|---|---|---|---|---|
|  | cyclodextrin |  |  |  |
| 30 plants |  |  |  |  |
| total length of the sprouts (mm.) | 55 | 33 | 336 | 319 |
| inhibition % | 82.8 | 89.6 |  | 0 |
| stimulation % |  |  | 14.7 | 0 |
| total length of the roots (mm.) | 3236 | 1991 | 4355 | 3492 |
| inhibition % | 7.3 | 43.0 |  | 0 |
| stimulation |  |  | 42.7 | 0 |

EXAMPLE 6

Growth inhibition of Triticale (strain No. 64) at +10° C.

The test is carried out as described in Example 5, using Triticale seeds. The data are shown in Table VI.

TABLE VI

|  | α | β | linear dextrin | control |
|---|---|---|---|---|
|  | cyclodextrin |  |  |  |
| 30 plants |  |  |  |  |
| total length of the sprouts (mm.) | 386 | 272 | 841 | 934 |
| inhibition % | 58.7 | 70.8 | 10.0 | 0 |
| total length of the roots (mm.) | 2254 | 1012 | 2891 | 3557 |

TABLE VI-continued

|  | α | β | linear |  |
|---|---|---|---|---|
|  | cyclodextrin | | dextrin | control |
| inhibition | 36.6 | 71.6 | 18.7 | 0 |

EXAMPLE 7

Growth inhibition of spring barley (Hordeum vulgare L. cv. 'MK 42') at +3° C.

The test is carried out as described in Example 5, but the sprout and root length of the seedling are measured in the dark after 14 days in a refrigerator of +3° C. The measured inhibition % are shown in Table VII.

TABLE VII

|  | α | β | linear |  |
|---|---|---|---|---|
|  | cyclodextrin | | dextrin | control |
| 30 plants total length of the sprouts | 2 | 2 | 59 | 20 |
| inhibition % | 90.0 | 90.0 | | 0 |
| stimulation | | | 195.0 | 0 |
| total length of the roots (mm.) | 94 | 111 | 1108 | — |
| inhibition % | 83.2 | 80.4 | | 0 |
| stimulation % | | | 98.2 | 0 |

EXAMPLE 8

Growth inhibition of anise (Pimpenella anisum L. cv. 'Budakalászi') at +28° C.

30—30 seeds are placed on a 3 cm. diameter Petri dishes and the seeds are wetted with 2.5 ml. of dextrin solution. The total length of the 7 day old seedlings was measured. 0% inhibition is the measured value of the control. The germ length of the seeds treated with various dextrins is inhibited as given in Table VIII.

TABLE 8

|  | α | β | linear |  |
|---|---|---|---|---|
|  | cyclodextrin | | dextrin | control |
| 30 plants total length (mm.) | 485 | 487 | 61 | 532 |
| inhibition % | 8.8 | 8.5 | 88.5 | 0 |

EXAMPLE 9

Growth inhibition of anise (Pimpinella anisum L. cv. 'Budakalászi') at +10° C. at 9 days The test is carried out as described in Example 8 but the seeds are germinated for 9 days in a refrigerator of +10° C. In Table IX the extent of inhibition is shown obtained when calculating the data of measuring the total length.

TABLE IX

|  | α | β | linear |  |
|---|---|---|---|---|
|  | cyclodextrin | | dextrin | control |
| 30 plants total length | 272 | 201 | 133 | 280 |
| inhibition % | 2.9 | 28.2 | 52.5 | 0 |

EXAMPLE 10

Anise (Pimpinella anisum L. cv. 'Budakalászi') growth regulation at +10° C. at 12 days The test described in Example 9 is evaluated at 12 days and the results are given in Table X.

TABLE X

|  | α | β | linear |  |
|---|---|---|---|---|
|  | cyclodextrin | | dextrin | control |
| 30 plants total length (mm.) | 492 | 435 | 248 | 332 |
| inhibition % | | | 25.4 | 0 |
| stimulation % | 48.2 | 31.0 | | 0 |

EXAMPLE 11

Inducing anti-dotum effect against pre-emergence herbicidal treatment in crops (green-house test)

Wheat, barley and triticale seeds were soaked for 24 hours at 28° C. in a $10^{-2}$ M solution according to the invention. After washing 10—10 seeds were sown three times into plastic vessels of a surface of 168 $cm^2$ filled with washed sand. After covering them the given dose of the herbicides was applied dissolved in 5 ml. of water pre-emergence by using aerosol spray. The damage of the plants caused by the herbicide was evaluated by weighing the plants at the age of 3 weeks when the symptoms have stabilized. The decreased extent of the damage after the treatment according to the invention (anti-dotum activity) may be seen from Table XI.

TABLE XI

| plant | green weight in the % of the untreated control | | plant | sprout | root |
|---|---|---|---|---|---|
| wheat | | βCD | 121 | 132 | 116 |
| | Dicuran 2 kg/ha | + βCD | 35 | 42 | 31 |
| | Dicuran | — | 28 | 29 | 27 |
| | Afalon 2 kg/ha | + βCD | 27 | 31 | 26 |
| | Afalon | — | 21 | 17 | 22 |
| | SD$_{5\%}$ 4.39 | | | | |
| triticale | | βCD | 29 | 111 | 142 |
| | Hungazin DT 6 kg/ha | + βCD | 57 | 59 | 55 |
| | Hungazin DT | — | 41 | 50 | 34 |
| barley | Hungazin DT 6 kg/ha | + βCD | 45 | 33 | 55 |
| | Hungazin DT | — | 32 | 22 | 39 |
| | SD$_{5\%}$ 8.04 | | | | |

EXAMPLE 12

Inducing anti-dotum effect against pre-emergence herbicidal treatment in corn (small parcel field trial) (Zea mays L. cv. 'Aranymazsola')

Corn seeds were sown as described in Example 11 into 5×3.5 m. parcels, 60 cm. of row distance and 40 cm. of stock distance. The sowing was repeated three times. The herbicide treatment was carried out directly after sowing pre-emergence by applying the given amount of the agent dissolved in water (500 l./ha) by using a sprayer. Four weeks after sowing the green-weight of the plants was measured after Afalon treatment and the detrimental effect of Hungazin DT was evaluated at the age of three months. The anti-dotum effect data are shown in Table XII.

TABLE 12

| treatment | | sprout green-weight in % of the untreated control |
|---|---|---|
| Hungazin DT 6 kg/ha | + βCD | 131 |
| Hungazin DT | — | 124 |
| — | βCD | 105 |
| Afalon 3 kg/ha | + βCD | 69 |
| Afalon | — | 55 |
| Afalon 5 kg/ha | + βCD | 54 |
| Afalon | — | 40 |
| | $SD_{5\%}$ 3.85 | |

What we claim is:

1. A method of controlling seed germination and seedling growth which comprises the step of contacting plant seeds with an effective amount of cyclodextrin solution or solid cyclodextrin selected from the group consisting of alpha-cyclodextrin, beta-cyclodextrin, gamma-cyclodextrin and mixtures of same in a composition containing 0.1 to 95% of cyclodextrin.

2. The method defined in claim 1 wherein the plant seeds are soaked with an aqueous solution of the cyclodextrin before sowing.

3. The method defined in claim 1 wherein the cyclodextrin is alpha-cyclodextrin.

4. The method defined in claim 1 wherein the cyclodextrin is beta-cyclodextrin.

5. The method defined in claim 1 wherein the cyclodextrin is gamma-cyclodextrin.